United States Patent [19]

Angstadt

[11] Patent Number: 4,699,214
[45] Date of Patent: Oct. 13, 1987

[54] SALT-TOLERANT ALKYL ARYL SULFONATE COMPOSITIONS FOR USE IN ENHANCED OIL RECOVERY PROCESSES

[75] Inventor: Howard P. Angstadt, Media, Pa.

[73] Assignee: Sun Refining and Marketing Company, Philadelphia, Pa.

[21] Appl. No.: 913,438

[22] Filed: Sep. 30, 1986

[51] Int. Cl.$^4$ .................... E21B 43/22; E21B 43/24
[52] U.S. Cl. ................................. 166/303; 252/8.554
[58] Field of Search .............................. 166/272, 303; 252/8.554

[56] References Cited

U.S. PATENT DOCUMENTS

| | | | |
|---|---|---|---|
| 1,981,337 | 11/1934 | Stoesser et al. | |
| 2,813,583 | 11/1957 | Marx et al. | 166/271 |
| 3,527,303 | 9/1970 | Zwicky | 166/303 |
| 3,880,237 | 4/1975 | Snavely, Jr. et al. | 166/272 X |
| 3,945,437 | 3/1976 | Chiu et al. | 166/275 X |
| 4,435,295 | 3/1984 | Stokke et al. | 252/8.554 |
| 4,458,759 | 7/1984 | Isaacs et al. | 166/303 X |
| 4,469,608 | 9/1984 | Hinkamp | 252/8.554 |
| 4,532,051 | 7/1985 | Nuckels et al. | 252/8.554 |
| 4,609,044 | 9/1986 | Lau | 166/272 X |

FOREIGN PATENT DOCUMENTS

| | | | |
|---|---|---|---|
| 1164889 | 4/1984 | Canada . | |
| 2557198 | 6/1985 | France | 252/8.554 |
| 85/05146 | 11/1985 | World Int. Prop. O. | 166/272 |

Primary Examiner—George A. Suchfield
Attorney, Agent, or Firm—J. Edward Hess; Donald R. Johnson; Stanford M. Back

[57] ABSTRACT

A process is provided for the enhanced recovery of oil with steam in reservoirs containing high concentrations of dissolved salts, wherein certain diaryl sulfonated surfactants are employed in conjunction with the steam which posses high tolerance for said salts. These surfactants are comprised of compositions having (1) two aromatic rings in their nucleus, such as diphenyl, diaryalkane, or naphthalene groups; (2) at least one alkyl group having 18 or more carbon atoms; and a second alkyl group having from 1-4 carbon atoms; and (3) two functional groups comprising at least one and preferably two sulfonate groups, although one of the sulfonate groups may be replaced with a carboxyl or hydroxyl groups. At least about 65% of the diaromatic compounds should contain two functional groups, preferably sulfonates, with the remainder comprising a monofunctional-substituted compound containing either a sulfonate group, a carboxylate group, or an hydroxyl group.

In a further embodiment of this invention, the diaryl sulfonated surfactants may be admixed with other co-surfactants and/or hydrotropes and silicates.

5 Claims, No Drawings

SALT-TOLERANT ALKYL ARYL SULFONATE COMPOSITIONS FOR USE IN ENHANCED OIL RECOVERY PROCESSES

BACKGROUND OF THE INVENTION

1. Field of the Invention

This invention relates to surfactant-enhanced oil recovery methods and compositions used therein wherein the surfactants employed are anionic surfactants. More particularly, this invention relates to the use of certain alkyl-substituted aryl sulfonates in enhanced oil recovery processes wherein the aryl moiety contains two aromatic rings, such as, for example, biphenyl, diarylalkane, or naphthalene groups which are substituted by at least two alkyl groups and at least two functional groups, as defined below, and wherein at least one of said functional groups is a sulfonate. These surfactants are particularly effective in conjunction with the use of steam in the enhanced recovery of subterranean oil, especially where there are present high aqueous concentrations of salts in the oil reservoirs. These surfactants, it has been found, are highly salt-tolerant and maintain their effectiveness even in the presence of divalent salts.

Many different classes of organic compounds are known to have surfactant properties, and a wide variety of these surfactants have been used for enhanced oil recovery. Since in most oil reservoirs there are found considerable amounts of water, and since this conate water frequently contains sizeable amounts of various salts dissolved in it, a very important property of any useful surfactant will be its ability to mobilize oil in saline environments. Anionic surfactant systems, including most alkylaromatic sulfonates, are excellent surfactants, but only at low salt concentrations. In the presence of dissolved salts, the hydrophilic portion of these molecules become less soluble because of the increased competition for water hydration molecules from the salt ions. Hence, as salinity increases surfactant solubility tends to decrease. The effect may be even more pronounced for salt solutions containing divalent cations. Therefore, it is an object of this invention to provide alkylaromatic sulfonates having tolerance for high concentrations of salts, particularly salts containing divalent cations, preferably for use in tertiary recovery systems employing steam rather than water.

2. Prior Art

Numerous patents address aqueous anionic surfactant systems for use in the secondary and tertiary recovery of oil from subterranean reservoirs. See, for example, U.S. Pat. Nos. 1,981,337; 3,469,630; 3,508,612; 3,811,504; 3,811,505; 3,811,507; or 3,945,437. See also, regarding arylsulfonates compounds per se, U.S. Pat. Nos. Re: 22,548; 2,368,361; 3,361,313; 4,172,029; as well as Okhmedov et al, Chem Abstr. 59, 15203H (1960); Moriga, Chem. Abstr. 70, 5421 N (1968); and Golikov et al, Chem Abstr. 76, 80291 c (1971).

In addition, Canadian Patent, No. 1,164,889 (1984) teaches the use of alkyl biphenyl disulfonates in the enhanced recovery of underground oil. However, this invention teaches (1) that preferably the biphenyl compounds be used as cosurfactants with petroleum sulfonates; (2) that the biphenyl compounds be at least 90% disulfonated; and (3) that the alkyl substituents be desirably monoalkyl with only a small amount of dialkyl compounds mixed in, wherein the alkyl group contains at least 6 carbon atoms and preferably 10-18 carbon atoms. As will be apparent from the following description of the present invention, the compounds of the Canadian patent and the compositions in which they are used in oil recovery methods differ in important ways from those claimed hereinbelow. Other differences between the other prior art compounds and methods and those claimed herein will likewise be evident from the following description.

SUMMARY OF THE INVENTION

In accordance with one embodiment of the present invention there is provided a process for the enhanced recovery of oil with steam in reservoirs containing high concentrations of dissolved salts, wherein certain alkyl aryl sulfonate surfactants which possess high tolerance for said salts are employed in conjunction with the steam. These surfactants are comprised of compositions having (1) two aromatic rings in their nucleus, such as diphenyl, diarylalkane, or naphthalene groups, (hereinafter "diaromatic compounds"); (2) two or more alkyl groups, at least one of which contains eighteen or more carbon atoms, desirably from about 18 to 40 carbon atoms, while the other has from about one to four carbon atoms; and (3) one or two functional groups, wherein at least 65 wt. % of the total composition contains two such groups, at least one of which, and preferably both, is a sulfonate group, while the other group may be a carboxylate, or sulfonate, or free acid thereof, or an hydroxyl group, while the remainder may contain a single functional group comprising a carboxylate, sulfonate, or free acid thereof, or an hydroxyl group. In the latter case the other functional group would be replaced by hydrogen.

These compositions may be depicted by the following formula:

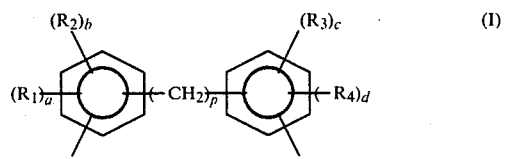

(I)

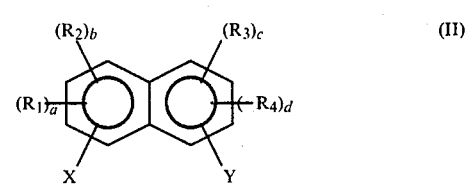

(II)

or mixtures thereof, wherein:

$R_1$ and $R_4$ are hydrogen or lower alkyl groups having from about 1-4 carbon atoms, wherein each of said R groups may be the same or different, with the proviso that at least one of said groups is lower alkyl;

$R_2$ and $R_3$ are hydrogen or alkyl groups having at least about 18 carbon atoms, desirably from about 18-40 carbon atoms, and preferably about 18-20 carbon atoms, in which the alkyl groups may be straight or branched, and wherein each of said R groups may be the same or different, with the proviso that at least one of said groups is alkyl;

X and Y are functional groups comprising an alkali metal sulfonate or carboxylate, or the free acid thereof, or an hydroxyl group; or hydrogen; with the proviso that at least about 65% by weight of the total composition must contain two such functional groups, at least one of which, and preferably both, must be a sulfonate, and with the further proviso that the remainder of the composition must contain a single functional group comprising an alkali metal sulfonate or carboxylate, the free acid thereof, or an hydroxyl group;

a, b, c, and d are each the integer 1 or 2, with the proviso that the sum of a and b, and the sum of c and d, is each never greater than 3;

p is the integer of 0–2; and the total number of carbon atoms in the alkyl side chains of the diaromatic moiety is at least about 19 carbon atoms, and preferably the total number of carbon atoms is from about 19 to 41.

From the foregoing description it will thus be seen that in at least 65% by weight of the composition the X and Y moieties comprise two functional groups, one of which must be a sulfonate, while the other group may be a sulfonate or carboxylate, or the free acid thereof, or an hydroxyl group. It will further be seen that the remainder of this total composition may comprise a monofunctional compound containing either a carboxylate, sulfonate, the free acid thereof, or an hydroxyl group, in which case the remaining X or Y group is hydrogen.

However, in a further embodiment of this invention, as will be described in more detail below, the above-defined diaromatic compounds may then desirably be admixed with other mono-functional co-surfactants, which themselves have salt-resistant properties, to form a surfactant mixture. As stated above, it is preferred that the final surfactant composition to be injected with the steam in tertiary recovery processes contain as high a content of difunctionalized diaromatics as possible, and most preferably at least about 65% by weight of difunctional diaromatics, preferably disulfonates. Nevertheless, when the diaromatic surfactant contains greater than about 65 wt. % difunctional compounds, it may be admixed with mono-functional co-surfactants up to about 35 wt. % of the final mixture, i.e., those amounts which will not reduce the amount of difunctional diaromatics below about the desired 65 wt. %. These co-surfactants themselves are desirably sulfonated, hydroxyl- and/or carboxyl-containing compounds, groups as described in further detail below.

This invention also contemplates the presence of other additives which may be used in combination with the above-described surfactants. Thus, for example, as described in further detail below, in addition to mono-functional co-surfactants, certain hydrotropes or silicates may also be added to the diaromatic surfactants of this invention in order to enhance their effectiveness. Additionally, conventional additives known in the art such as stabilizers, antibacterial agents and the like may also be included. These additives may be included to the extent that they do not adversely affect the salt-resistant properties obtained by the surfactants of this invention.

DESCRIPTION OF THE INVENTION

As aforestated, the present invention involves the use of steam recovery processes for the tertiary recovery of oil from underground formations wherein there are introduced with the steam effective amounts of surfactants comprising the dialkyl diaryl sulfonate compounds of structures I or II, or mixtures thereof, as defined above, with or without co-surfactants and/or other additives.

These diaromatic surfactants, which have been found to be especially tolerant of salt concentrations found in aqueous systems associated with underground formations, and particularly salts containing divalent cations, can readily be administered by introducing them with the steam in the form of aqueous solutions of the surfactants.

The amount of the surfactant composition of this invention admixed with the steam may vary widely according to the characteristics of the formation, and is not critical, but desirably the weight of the surfactant in the steam should be in the range of from about 0.1 to 10 wt. %, and preferably about 0.5–5 wt. %, based on the weight of the water equivalent of the steam. This concentration, in turn, may be achieved by metering the composition into the steam from a more concentrated solution.

The surfactants defined by structures I and II above, i.e., compounds whose nucleus contain two aromatic rings, comprising either biphenyl, diarylalkane, or naphthalene moieties, may readily be prepared by generally known methods wherein said aromatic nucleus, or nuclei, is first alkylated to the extent necessary to provide a compound having a total of at least about 19 carbon atoms in the alkyl side chains, and thereafter is sulfonated, and optionally hydroxylated or carboxylated, to provide the desired product. Additionally, if desired, alkali metal salts, including ammonium salts, of the sulfonic and/or carboxylic acid may thereafter be formed by conventional neutralization processes.

Where compounds having hydroxyl and/or carboxyl groups are desired in addition to the sulfonate groups, the aryl starting materials may conveniently be carboxylated or hydroxylated by known means or, more preferably, selected from readily available materials which already contain these substituents, as for example hydroxynaphthalene, naphthalene carboxylic acids, biphenyl carboxylic acids, hydroxybiphenyl, hydroxyphenylphenylmethane and the like.

Similarly, in order to provide surfactants containing lower alkyl groups having from 1 to 4 carbon atoms in addition to one or more long chain alkyl groups, i.e. those containing 18 or more carbon atoms, the aryl starting material may readily be selected from known lower alkyl-substituted aryl compounds such as methylnaphthalene, diethylnaphthalene, methylbiphenyl, polymethylbiphenyl, hydroxymethylnaphthalene, tolyl phenylmethene, methylbiphenyl, ditolymethane, and the like, which may then be alkylated with long-chain alkyl groups as described above, and thereafter sulfonated.

As will be evident from the structures of compounds I and II above, it is essential that the final surfactant product contain, in addition to at least one short chain alkyl group, at least one long chain alkyl group having about 18 or more carbon atoms, desirably either straight or branch-chain alkyl groups having from about 18 to 40 carbon atoms, and most preferably an average of from about 18 to 20 carbon atoms. The term "average" is meant to signify that the alkyl moiety may be derived from mixtures of hydrocarbons having a weighted average of from about 18 to 20 carbon atoms, even though somewhat shorter or longer chain lengths may be present in the mixture. Thus, in one preferred embodiment of the invention, the long-chain alkyl moiety may be derived from a mixed $C_{18-20}\alpha$-olefin source in which the molecular weight distribution is such that the resultant alkyl side chain has an average of about 18 carbon atoms, even though lesser amounts of somewhat shorter or longer chain lengths may be present in the alkylated product. Alternatively, pure olefins having exactly the desired number of carbon atoms within this range may also be employed.

In addition to the dialkyl diaromatic sulfonates there may, as described above, be employed as co-surfactants in the compositions of this invention such compounds as petroleum sulfonates. The petroleum sulfonates encompass a broad range of compounds which are well known in the art, and which are generally obtained by the sulfonation of naturally occurring petroleum streams derived from crude oil. Typical of this broad range are those petroleum sulfonates described in U.S. Pat. Nos. 3,302,713; 3,508,612; 3,648,772; and 3,901,317 all of which are incorporated herein by reference.

Thus, the term "natural petroleum sulfonates" is a commercial designation of petroleum sulfonates which are obtained by a treatment of petroleum fractions, particularly solvent-treated aromatic fractions, with, for example, sulfuric acid, fuming sulfuric acid, or sulfur trioxide. Upon sulfonation two types of general products are thereby formed which are known in the art as mahogany acid sulfonates and green acid sulfonates, respectively, based on their color and solubility in oil or water.

A second type of co-surfactant which may be used in the compositions disclosed herein are $\alpha$-olefin sulfonates which are generally commercially available materials, as for example those obtained from olefins made by the "SHOP" process available from Shell Oil Co. Typically these olefins may have the following structures:

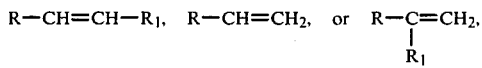

wherein R and $R_1$ may be hydrogen, or alkyl groups having from 8–28 carbon atoms, and may be the same or different. Preferred amongst these are those alkyl groups having from about 10 to 16 carbon atoms. While the methods for preparing these compounds are generally well known, the olefin sulfonates may best be described as the sulfonation products of wax-cracked hydrocarbons having from about 12 to 30 carbon atoms, or alternatively of ethylene oligomers, e.g., those obtained by Ziegler-type polymerizations, and having from about 12 to 30 carbon atoms. Also contemplated within the scope of the invention are known derivatives of said olefin sulfonates such as ether sulfonates, ethoxylated sulfonates, or propoxylated sulfonates. In general, these compounds may be prepared by well-known procedures.

Finally, among the co-surfactants which may desirably be employed in the compositions of the invention are alkylaryl sulfonates having at least one long chain alkyl group containing from 12 to 30 carbon atoms, preferably from 14 to 20 carbon atoms, and optionally a short chain alkyl group having from 1 to 4 carbon atoms. Included amongst these compounds are alkyl benzenes sulfonates, alkyl xylene sulfonates, alkyl toluene sulfonates and the like, wherein the alkyl side chain may be derived from a $C_{12-30}$-olefin source, preferably one having an average of $C_{14-20}$ carbon atom chain.

The amount of co-surfactants, if any, which may be employed together with the dialkyl diaromatic surfactants described above may vary considerably, but in any event should not exceed that amount which will reduce the content of the defunctionalized diaromatics below about 65 wt. % of the final surfactant composition.

The alkylation of aryl compounds to form the polyalkyl diaromatics of this invention is well known in the art, and various methods may readily be employed. Thus, for example, such starting compounds as methylbiphenyl, dimethylbiphenyl, methylnaphthalene, dimethylnaphthalene, ditolylmethane, and the like, including those containing lower alkyl, carboxyl, or hydroxy groups may be alkylated with any of the aforedescribed long chain hydrocarbons having at least about 18 carbon atoms by reacting the corresponding halogenated hydrocarbon, or the corresponding $\alpha$-olefin, in the presence of an appropriate catalyst such as $AlCl_3$, HF, or $HF-BF_3$.

The degree of alkylation, i.e. the number of short and/or long-chain alkyl groups introduced into the aryl nucleus, may readily be controlled in a known manner by varying the ratios of reactants or the like. That is to say, where at least one long chain alkyl group monoalkylation is desired, large excesses of aryl compound over alkylating agent are essential, preferably in molar ratios of from about 10:1–20:1. On the other hand, if polyalkylation is desired the ratios of aryl compound over alkyl may be significantly reduced or even reversed, i.e. molar ratios of from about 2:1–1:2 may be employed.

Of the several dialkyl or polyalkyl aryl compounds which may thus be prepared for use in the processes of this invention, those containing a single long and short-chain (i.e. lower alkyl) group, are preferred. Thus, for example, such compounds as $C_{18}$-methylbiphenyl, $C_{18}$-methylnaphthalene, $C_{18}$-diphenylmethane, $C_{18}$-ditolylmethane, and the like, when sulfonated, represent the surfactants of choice in carrying out this oil recovery method.

The sulfonation, and particularly disulfonation, may be readily achieved in various ways, as for example by direct vapor-phase sulfonation with sulfur trioxide in a falling film reactor; with liquid $SO_2$-$SO_3$ sulfonation; with solvent $-SO_3$ sulfonation; or using sulfuric acid-oleum sulfonation, all of which processes are known in the art.

The sulfonic acid, and where present the carboxylic acid, may desirably be converted to the corresponding alkali metal or ammonium salt, including substituted ammonium salts such as ethylammonium, propylammonium, methylammonium, and the like. This is readily accomplished by known methods by reacting the acid with an alkali metal hydroxide, $NH_3$, a substituted ammonium compound or the like to form the desired salt, preferably the sodium or potassium salt, followed, if desired, by drying the reaction medium to recover the diaromatic sulfonate product.

These compounds, when dissolved in, e.g., water, and injected with steam, are highly effective when used alone in high salt environments. Optionally, as stated above, these surfactants may also be used with other additives which further enhance their effectiveness. Thus, for example, in addition to minor amounts of stabilizers, bacteriostats, anti-oxidants and the like commonly used in oil recovery compositions, as well as the aforedescribed co-surfactants, there may also be employed compounds known as hydrotropes, i.e. those compounds characterized in the art by their ability to increase the solubility of surfactants in aqueous systems.

See, for example, the description in "Synthetic Detergents", Davidsohn et al, 6th Ed., Wiley and Sons, pages 79, 80. Included amongst these compounds are both aryl and non-aryl compounds. The aryl compounds are generally aryl sulfonates or short chain alkyl aryl sulfonates in the form of their alkali metal salts, in which there may be present from 1 to 3 alkyl groups, each containing from 1 to about 3 carbon atoms, and in which the aryl component may be benzene, naphthalene, or such alkyl-substituted aryl compounds as toluene, xylene, or cumene. Included amongst these aryl hydrotropes are such preferred compounds as sodium xylene sulfonate, sodium toluene sulfonate, sodium benzene sulfonate, sodium naphthalene sulfonate, and the like. Non-aryl hydrotropes which may likewise be satisfactorily employed included such compounds as sodium isethionate, butane sulfonate, hexane sulfonate, and the like, i.e., sulfonates whose alkyl moiety contains from about 1 to 8 carbon atoms.

Another additive which may be used with the surfactants of this invention is, as afore-described, an alkali metal silicate. These silicates are available in a wide range of compositions which are generally referred to and defined by the ratio of silica, to alkali metal oxide, i.e., by the weight ratio of $SiO_2/M_2O$, where M is an alkali metal. This ratio is not a fixed quantity and may vary greatly depending upon the quantities of metal oxide and silica employed. Thus, a wide range of silicate compositions may be formed and used in enhancing the effectiveness of the surfactants of this invention. It is generally preferred to use those silicates which have a relatively high proportion of silica, e.g. those silicates having a weight ratio of $SiO_2/M_2O$ of about 0.5 to 4.0, preferably about 1.5 to 3.3, wherein M is an alkali metal, such as sodium, potassium, or lithium. Examples of these silicates included alkali metal orthosilicates, alkali metal metasilicates, alkali metasilicate pentahydrates, and alkali metal sesquisilicates. Particularly useful are silicates such as sodium and potassium orthosilicate, sodium and potassium metasilicate, sodium and potassium metasilicate pentahydrate, and sodium and potassium sesquisilicate.

These alkali metal silicates may conveniently be prepared by adding caustic to an aqueous solution of an alkali metal silicate having a $SiO_2/M_2O$ weight ratio of more than 1. Alternatively, they may be obtained commercially in pre-prepared ratios of $SiO_2/M_2O$ of, for example, 1.6; 2.4; 3.2 and the like, such as those made available by PQ Corp. under the trademark ACOR (E-Series).

As with the co-surfactants, the amounts of hydrotropes, silicates on mixtures thereof may vary widely but in any event should not exceed that amount which will reduce the content of the disulfonated dialkyl diaromatics below about 50 wt. % of the final surfactant composition. More preferably, these optional additives should be present in amounts not exceeding about 20 wt. % of the total composition, with the balance comprising either the diaromatics alone or in admixture with suitable amounts of co-surfactants. Where a mixture of both hydrotropes and silicates are employed, they should desirably be present in weight ratios of about 1:1, although this ratio is not critical.

The steam recovery process may be carried out either as a cyclic process or a steam drive process, and the heavy crude oil recovered in a generally well-known manner. Thus, in a typical cyclic steam process oil is produced from the same well from which the steam was previously added, while in a typical steam drive process the oil production well is remote from the steam injection well.

The following examples are provided to illustrate, but not limit, the scope of this invention.

EXAMPLE 1

The following procedure illustrates the preparation of a typical alkylaryl biphenyl compound employed in the process of this invention.

Purified biphenyl is dissolved in n-hexane solvent at the ratio of 500 ml of hexane/mole of aromatic and charged to a stirred reaction vessel. Two weight percent (based upon olefin feed) of an aluminum chloride/aromatic/ methylchloride complex is added to this solution, and the entire contents is heated to 50°–60° C. Sufficient dry $C_{18}\alpha$-olefin is then added over 1–1½ hrs. so that the final olefin/aromatic molar ratio was 0.2. After the olefin addition the reactor is stirred an additional five minutes at reaction temperature. The reaction product is cooled to room temperature and the complex neutralized using 5 volume percent of 1 to 2 N sodium hydroxide. After washing the organic layer with distilled water several times and drying the organic layer, the solvent is removed and the product $C_{18}$-alkylbiphenyl is obtained by vacuum distillation. An alkylation yield of about 85 wt. % monoalkylate is attained. In a similar known manner the short chain alkyl group or groups may then be introduced into the diaromatic nucleus.

Alternatively, in accordance with the foregoing procedure, but substituting methylbiphenyl for biphenyl, the corresponding $C_{18}$-alkylmethylbiphenyl is obtained.

EXAMPLE 2

The following procedures illustrates the sulfonation of, for example, the alkylbiphenyl compounds of Example 1.

In a typical solvent sulfonation to prepare alkylbiphenyl sulfonate, $SO_3$ entrained in a stream of nitrogen is bubbled through a hexane solution of the appropriate alkylate at ambient temperature. From about 0.25 to 0.5 moles of aklylate are added to an equal weight of hexane in an indented Morton flask equipped with a mechanical stirrer, condenser, bubbler tube and thermometer. A 5 to 10 percent excess of twice the stoichiometric amount of liquid $SO_3$ is placed in an $SO_3$ evaporator for entrainment in a stream of nitrogen flowing to the bubbler tube. The rate of $SO_3$ evaporation is controlled to complete the $SO_3$ addition in 3 to 8 hours. An ice bath is used to maintain the reaction flask at 25° C.

Upon completion of the reaction, hexane solvent is removed by evaporation to constant weight in a rotary evaporator under vacuum with a water aspirator. The sulfonation produces a product assaying in the range of 70–90 percent disulfonic acid with alkyl biphenyl alkylates. Standard neutralization with sodium hydroxide solution provides a sulfonate product, the activity of which depends upon the extent of sulfonation obtained and the concentration of the sodium hydroxide used for neutralization, usually in the range of 15–50 percent.

EXAMPLE 3–5

In the following examples, the method used to evaluate the usefulness of the composition comprised packing a tube having a diameter of 2″ and a length of 18″ with oil-saturated 140-mesh Ottowa sand. The water-wet sand was coated with Midway Sunset crude oil to between 60–65% residual oil saturation. The top 15% of the tube was filled with clean sand to simulate a zone of oil recovered based upon the amount of oil originally in place in the pack is summarized in Table II below.

TABLE II

| Example | Surfactant | Composition (Surfactant) (WT. %) | Salinity (% NaCL) | Recovery (% OOIP) |
|---|---|---|---|---|
| 6 | $C_{18}$ alkyl methyl biphenyl DS[a] | 100 | 15 | 75 |
| 7 | $C_{18}$ alkyl dimethylnaphthalene DS | 100 | 15 | 70 |
| 8 | Steam alone | — | 15 | 44.5 |

[a]DS = disulfonate high permeability frequently found in steamed reservoirs. The tube was insulated to reduce heat losses, and then either a 40–50% quality steam alone, i.e. that proportion if the water in vapor form, or a 40–50% quality steam in combination with various surfactant systems was passed through the sand pack diluted to concentrations of 1 weight percent surfactant based on the weight of the water equivalent of the steam at appropriate rates until no more oil was evident exiting from the apparatus. The amount of oil recovered was measured in one or both of two ways: (1) total liquid oil obtained from the pack; or (2) the oil remaining on the sand at the end of the experiment was determined, and the amount recovered calculated as the difference from the value determined to be on the sand at the start of the experiment. The percent of oil recovered based on the amount of oil originally in place in the pack, is summarized in Table I below.

In each of these examples 9.3 cc (100% surfactant-active basis) of an alkyl biphenyl sulfonate whose alkyl moiety contained an average of 18 carbon atoms was diluted with water to provide a final concentration of 1 wt. % of surfactant in the steam (based on the weight of its water equivalent).

In addition, a series of runs was made with steam alone for purposes of comparison. The average percent recovery from these runs is reported in Example 3.

TABLE I

| EXAMPLE | SURFACTANT | RECOVERY (% OOIP)[d] |
|---|---|---|
| 3 | — | 44.5[a] |
| 4 | $C_{18}$ Sursol-177[b] | 78.7 |
| 5 | $C_{18}$ Sursol-175[c] | 79.8 |

[a]steam alone-average recovery from 8 runs
[b]$C_{18}$ Sursol 177-(available from Koch Industries, Inc., Wichita, KS)
[c]$C_{18}$ Sursol 175-(available from Koch Industries, Inc., Wichita, KS)
[d]OOIP - original oil in place The composition of Sursol 175 and Sursol 177 employed in the above examples is as follows:

| COMPONENT (WT. %) | SURSOL 177 | SURSOL 175 |
|---|---|---|
| Lighter than biphenyl | 1–5 | 0 |
| Biphenyl | 10–20 | 5 |
| Methylbiphenyl | 50–60 | 80–85 |
| Biphenylmethane | — | 3 |
| Others (polyalkylaromatics) | 15–30 | 7–20 |
| Aromatic components | 100 | 100 |

EXAMPLES 6–8

The method used to evaluate the utility of the compositions of these examples was similar to that of Examples 3–5 except that the residual water in the sand pack was composed of brine solutions to simulate the conate water of high salt containing reservoirs. Evaluation of the effect of the surfactants was the same. The percent

EXAMPLE 9

In accordance with the procedure of Example 7, but substituting $C_{18}$ for dimethylnaphthalene, the original oil in place is removed in high yield.

EXAMPLE 10

In accordance with the procedures of Example 6, but substituting a mixture of $C_{18}$-Sursol-175 disulfonate and a $C_{16}$-toluene sulfonate co-surfactant in a wt. % ratio of 70:30, the original oil in place is recovered in high yield.

Similarly, when a 65:35 wt. % mixture of $C_{18}$-Sursol-175 disulfonate and the co-surfactant $C_{16}$-α-olefin sulfonate are employed, there is obtained recovery of the original oil in place in good yield.

In accordance with the foregoing procedures, but substituting a 65:35 wt. % mixture of $(C_3)_6$-methyl-biphenyl disulfonate and the co-surfactant $C_{18}$-toluene sulfonate, recovery of the original oil in place in good yield is likewise obtained.

What I claim is:

1. A process for the recovery of the oil from subterranean reservoirs which comprises injecting together with steam an effective amount of a alkylated diaromatic sulfonated surfactant composition of the formula

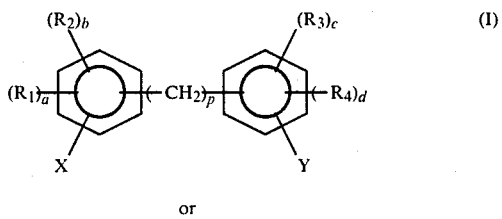

or

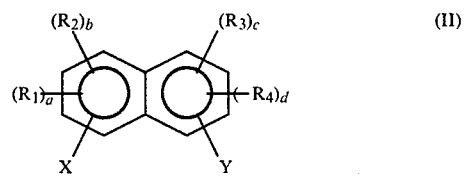

or mixtures thereof, wherein:

$R_1$ and $R_4$ are hydrogen or lower alkyl groups having from about 1–4 carbon atoms, wherein each of said R groups may be the same or different, with the proviso that at least one of said groups is lower alkyl;

$R^2$ and $R_3$ are hydrogen or alkyl groups having at least about 18 carbon atoms, in which the alkyl groups may be straight or branched, and wherein each of said R groups may be the same or different, with the proviso that at least one of said groups is alkyl;

X and Y are functional groups comprising an alkali metal sulfonate or carboxylate, or the free acid thereof, or an hydroxyl group; or hydrogen; with the proviso that least about 65% by weight of the total composition contains two such functional groups, at least one of which must be a sulfonate, and with the further proviso that the remainder of the composition contains a single functional group comprising an alkali metal sulfonate or carboxylate, the free acid thereof, or an hydroxyl group;

a, b, c, and d are each the integer 1 or 2, with the proviso that the sum of a and b, and the sum of c and d, is each never greater than 3;

p is the integer of 0–2; and the total number of carbon atoms in the alkyl side chains of the diaromatic moiety is at least about 19 carbon atoms, and recovering the oil from said reservoirs.

2. The process of claim 1 wherein the surfactant is a biphenyl, diarylalkane, or naphthalene compound.

3. The process of claim 1 further comprising that the diaromatic surfactant is admixed with a petroleum sulfonate, alkylaryl sulfonate, or α-olefin sulfonate co-surfactant, or mixture thereof, with the proviso that the weight percent of difunctional diaromatic surfactant in the final mixture is at least about 65 wt. %.

4. The process of claim 1 or 2 further comprising that the sulfonated surfactant is admixed with a hydrotrope or alkali metal silicate, or mixture thereof, with the proviso that the weight percent of difunctional diaromatic surfactant in the final mixture is at least about 65 wt. %.

5. The process of claim 1 wherein the the total number of carbon atoms in the alkyl side chains is from 19 to about 41.

* * * * *